United States Patent [19]

Chu et al.

[11] Patent Number: 4,486,616

[45] Date of Patent: Dec. 4, 1984

[54] REJUVENATION OF DESELECTIVATED ALKYLATION CATALYST

[75] Inventors: Chin-Chiun Chu, North Brunswick; Warren W. Kaeding, Westfield, both of N.J.

[73] Assignee: Mobil Oil Corporation, New York, N.Y.

[21] Appl. No.: 493,853

[22] Filed: May 12, 1983

Related U.S. Application Data

[63] Continuation of Ser. No. 102,729, Dec. 13, 1979, abandoned.

[51] Int. Cl.$^3$ .................. C07C 2/68; B01J 29/38; B01J 29/28
[52] U.S. Cl. ...................... 585/466; 502/28; 502/34; 502/77; 502/85; 585/467; 585/475
[58] Field of Search ........... 252/413, 414, 412, 411 R, 252/437, 455 Z; 585/466, 467, 471, 475; 502/28, 34, 77, 85

[56] References Cited

U.S. PATENT DOCUMENTS

| | | | |
|---|---|---|---|
| 3,493,490 | 2/1970 | Plank et al. | 252/412 |
| 3,684,738 | 8/1972 | Chen | 252/412 |
| 4,001,346 | 1/1977 | Chu | 585/467 |
| 4,002,698 | 1/1977 | Kaeding | 252/411 R |
| 4,011,276 | 3/1977 | Chu | 585/471 |
| 4,088,706 | 5/1978 | Kaeding | 585/412 |
| 4,098,837 | 7/1978 | Chu | 585/471 |
| 4,128,592 | 12/1978 | Kaeding | 585/466 |
| 4,137,195 | 1/1979 | Chu | 252/455 Z |
| 4,420,418 | 12/1983 | Chu | 502/77 |

*Primary Examiner*—P. E. Konopka
*Attorney, Agent, or Firm*—A. J. McKillop; Michael G. Gilman; Edward F. Kenehan, Jr.

[57] ABSTRACT

A process for alkylation of aromatic hydrocarbon reactants to dialkylbenzene products, whereby chemically modified zeolite catalysts are treated with an organic acid to enhance their intrinsic para-selectivity in the alkylation reaction. The modified zeolites which may be so reselectivated or improved comprise those crystalline zeolites having a constraint index of 1 to 12, a silica to alumina mole ratio of at least 12, and having a minor proportion of the oxide form of one or more chemical elements (e.g. phosphorus and magnesium) deposited thereon.

20 Claims, No Drawings

REJUVENATION OF DESELECTIVATED ALKYLATION CATALYST

This is a continuation of copending application Ser. No. 102,729, filed Dec. 13, 1979, now abandoned.

BACKGROUND OF THE INVENTION

1. Field of the Invention

This invention relates to alkylation catalysts. It is particularly concerned with a novel type of zeolite catalysts which exhibit a high degree of para selectivity in alkylation and transalkylation reactions.

2. Description of the Prior Art

Zeolite catalysts which have been modified by deposition thereon of a small amount of magnesium and phosphorus are known to promote the alkylation of aromatic compounds with a high degree of selectivity to the para isomer of the dialkylated benzene. See, for example, U.S. Pat. Nos. 4,011,276 and 4,098,837 to C. Chu and U.S. Pat. No. 4,128,592 to W. W. Kaeding.

Unfortunately, it has been found that the desirable para selectivity of these very unusual and useful catalysts can be adversely affected (i.e. the catalyst is "deselectivated") during normal use and storage. While the overall alkylation and disproportionation activity of the catalyst is generally unaffected, the selectivity to the desired para isomer in the product is reduced dramatically. Attempts to regain the para selectivity by conventional methods, such as drying and calcining to remove adsorbed water from the deselectivated catalyst, have been unsuccessful.

SUMMARY OF THE INVENTION

It has now been found that the deselectivated chemically modified zeolite alkylation catalysts may be rejuvenated, i.e. reselectivated, by treatment with an organic acid in either the vapor or the liquid phase. The catalysts with which this invention is concerned comprise a unique type of crystalline zeolite which is characterized by a silica to alumina mole ratio in excess of 12 and a constraint index, as hereinafter defined, within the approximate range of 1 to 12. These catalysts, after being chemically modified by the addition thereto of a minor proportion of the oxide form of one or more chemical elements (such as with an oxide of phosphorus and an oxide of magnesium) show a very high level of selectivity to para isomer in the production of dialkylbenzenes.

Generally, the invention comprises contacting the deselectivated oxide-modified zeolite catalyst with an organic acid, preferably acetic acid, for a relatively short length of time and then drying and calcining the rejuvenated catalyst. Contact may be carried out in situ by passing a stream of air, saturated with the organic acid, across the catalyst bed at a temperature of from about 0° C. to about 100° C., and preferably at between about 15° C. and 100° C. Alternatively, the deselectivated catalyst may be contacted with liquid organic acid at a temperature of about 0° C. to about 100° C., and preferably at 15° C. to 100° C.

Another embodiment of this invention involves increasing the selectivity of an oxide-modified zeolite catalyst which exhibits only moderate threshold selectivity to the para isomer. By contacting such catalysts with an organic acid prior to use it is frequently possible to upgrade the degree of para-selectivity to significantly higher levels.

DESCRIPTION OF SPECIFIC EMBODIMENTS

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with an oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra. Briefly, the preferred type zeolites useful in this invention possess, in combination: a silica to alumina mole ratio of at least about 12 and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. In addition, zeolites as characterized herein which are substantially free of aluminum, i.e. having silica to alumina mole ratios of 1,600 and higher, are found to be useful and even preferable in some instances. Such "high silica" zeolites are intended to be included within this description. The preferred zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although it is thought that 12-membered rings usually do not offer sufficient constraint to produce advantageous conversions, it is noted that the puckered 12-ring structure of TMA offretite does show constrained access. Other 12-ring structures may exist which may be operative and, therefore, it is not the present intention to judge the usefulness herein of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| ZEOLITE | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a zeolite when determined by any combination of conditions within the testing definition set forth hereinabove to have a Constraint Index of 1 to 12 is intended to be included in the instant catalyst definition regardless that the same identical zeolite, when tested under other of the defined conditions, may give a Constraint Index value outside of 1 to 12.

The class of zeolites defined herein is exemplified by ZSM-5, ZSM-11, ZSM-12, ZSM-23, ZSM-35, ZSM-38, and other similar materials.

Zeolite catalyst ZSM-5 is described in greater detail in U.S. Pat. Nos. 3,702,886 and 3,941,871. The entire descriptions contained within those patents, particularly the X-ray diffraction pattern of therein disclosed ZSM-5, are incorporated herein by reference.

The zeolite ZSM-11 is described in U.S. Pat. No. 3,709,979. That description, and in particular the X-ray diffraction pattern of said ZSM-11, is incorporated herein by reference.

Synthetic zeolite ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed catalyst, is incorporated herein by reference.

ZSM-35 is described in U.S. Pat. No. 4,016,245. The description of that catalyst, and particularly the X-ray diffraction pattern thereof, is incorporated herein by reference.

Zeolite ZSM-38 is more particularly described in U.S. Pat. No. 4,046,859. The description of that catalyst, and particularly the specified X-ray diffraction pattern thereof, is incorporated herein by reference.

It is to be understood that by incorporating by reference the foregoing patents to describe the preferred catalysts with greater particularity, it is intended that identification of the therein disclosed crystalline zeolites be resolved solely on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the silica-alumina mole ratios discussed therein. It is the crystal structure, as identified by the X-ray diffraction "fingerprint", which establishes the identity of the crystalline zeolite catalyst.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to this type zeolite catalyst by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35 and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the desired conversion process, it may be desirable to incorporate the above-described crystalline zeolite with another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels, including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

Prior to use the zeolite catalysts contemplated herein are chemically modified to render them para selective in reactions involving the alkylation or transalkylation of aromatic compounds, or to enhance any inherent para selectivity the zeolite itself may possess. Modification involves impregnation of the zeolite crystal with a compound of an element known to enhance para selectivity, followed by heating in air to convert the element to its oxide form. Non-limiting examples of elements which, when incorporated into the zeolite in an oxide form, are known to "selectivate" the catalyst (i.e. enhance the para selectivity) include antimony, arsenic, boron, calcium, magnesium, nickel, phosphorus, uranium, zinc and others. These elements, in their various oxide forms, may be used alone or in combinations. Combinations are preferred, and particularly combinations of an oxide of phosphorus together with oxides of one or more of the metallic elements. A particularly preferred embodiment of the invention involves the reselectivation of a zeolite catalyst which has been chemically modified by the addition thereto of a minor proportion of an oxide of phosphorus and a minor proportion of an oxide of magnesium. Such embodiment, that is a Mg.P-modified zeolite, shall henceforth be employed to further illustrate the invention. It should be understood, however, that such embodiment is intended to be representative of the invention and that other chemically modified zeolites known to exhibit desirable para selectivity in alkylation and transalkylation reactions may likewise benefit from practice of the herein disclosed invention.

The crystals of zeolite in a form substantially free of alkali metal, i.e. containing less than about 1.5 weight percent alkali metal and preferably having at least a portion of the original cations associated therewith replaced by hydrogen, are brought into contact with a phosphorus compound so that such compound may be absorbed thereon. Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=S$, $RPO_2$, $PRS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2RSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphonates, $(RO)P(O)R_2$; phosphinous acids, $R_2POX$, such as diethylphosphinous acid, primary, $(RO)P(OX)_2$, secondary, $(RO)_2POX$, and tertiary; $(RO)_3P$, phosphites; and esters thereof such as the monopropyl ester, alkyl dialkylphosphinites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include ammonium dihydrogen phosphate, diammonium hydrogen phosphate, diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid, such compound may be in solution in a suitable solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The phosphorus-containing compound may also be used without a solvent, i.e., may be used as a neat liquid. Where the phosphorus-containing compound is in the gaseous phase, such as where gaseous phosphorus trichloride is employed, the treating compound may be used by itself or in admixture with a gaseous diluent which is relatively inert to the phosphorus-containing compound and the zeolite (such as air or nitrogen) or with an organic solvent (such as octane or toluene).

Prior to reacting the zeolite with the phosphorus-containing compound, the zeolite may be dried. Drying can be effected in the presence of air and elevated temperatures may be employed. However, the temperature should not be such that the crystal structure of the zeolite is destroyed.

Heating of the phosphorus-impregnated catalyst subsequent to preparation and prior to use is also preferred. The heating can be carried out in the presence of oxygen—for example, in air. Heating can be at a temperature of about 150° C., although higher temperatures, e.g., up to about 500° C., are preferred. Heating is generally carried out for 2-5 hours but may be extended to 24 hours or longer. While temperatures of above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the zeolite is combined with a binder, e.g. 35 weight percent of alumina. The amount of phosphorus can be as high as about 25 percent by weight or more depending on the amount and type of binder present. Preferably, the amount of phosphorus added to the zeolite is between about 0.5 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus will be incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction with the treating compound, and the amount and type of binder incorporated with the zeolite.

The zeolite, containing phosphorus oxide, may then be further combined with magnesium oxide by contact with a suitable compound of magnesium, so that such compound may likewise be absorbed thereon. Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid, such compound may be in solution in a suitable solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it may be used by itself or in admixture with a gaseous diluent which is relatively inert to the treating compound and the zeolite (such as helium or nitrogen) or with an organic solvent (such as octane or toluene).

Heating of the magnesium compound impregnated catalyst subsequent to preparation and prior to use is preferred. The heating can be carried out in the presence of oxygen—for example, in air. Heating can be at a temperature of about 150° C., although higher temperatures, e.g. up to about 500° C., are preferred. Heating is generally carried out for 1-5 hours but may be extended to 24 hours or longer. While temperatures of above about 500° C. may be employed, they are generally not necessary. After heating in air at elevated temperatures, the oxide form of magnesium is present.

The amount of magnesium oxide incorporated in the calcined phosphorus oxide-impregnated zeolite should be at least about 0.25 percent by weight. However, it is preferred that the amount of magnesium oxide in the zeolite be at least about 1 percent by weight, particularly when the zeolite is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

The amount of magnesium oxide incorporated with the zeolite by reaction with the treating solution and subsequent calcination in air will depend on several factors. One of these is the reaction time, i.e. the time that the zeolite and the magnesium-containing source are maintained in contact with each other. With greater reaction times, all other factors being equal, a greater amount of magnesium oxide will be incorporated with the zeolite. Other factors upon which the amount of magnesium oxide incorporated with the zeolite is dependent include reaction temperature, concentration of the treating compound in the reaction mixture, the degree to which the zeolite has been dried prior to reaction with the treating compound, the conditions of drying of the zeolite after reaction with the magnesium compound, and the amount and type of binder incorporated with the zeolite.

After contact of the phosphorus oxide-containing zeolite with the magnesium reagent, the resulting composite is dried and heated in a manner similar to that used in preparing the phosphorus oxide-containing zeolite.

The afore-described Mg.P modified zeolite catalyst is useful in promoting alkylation reactions and disproportionation reactions of aromatic compounds and to maximize the yield of the para isomer of the dialkylbenzene component of such reactions. Examples of these reactions and suitable conditions therefor are disclosed in U.S. Pat. Nos. 4,011,276, 4,098,837 and 4,128,592, all of which are incorporated herein by reference.

It has been found that these catalysts will frequently lose a significant proportion of their desirable para selectivity after a relatively short period of use and sometimes even during extended storage prior to use. This deterioration of para selectivity (deselectivation) of the catalyst frequently occurs even though the overall catalytic activity of the chemically modified zeolite is not appreciably decreased.

We have found that these deselectivated catalysts can be rejuvenated and their useful lives significantly extended by bringing the catalyst into contact with an organic acid. The organic acid may be either in the vapor phase or in the liquid phase. If in the vapor phase, treatment is preferably carried out by passing a stream of air or nitrogen or other gaseous substance (argon, methane, pentane, etc.) which has been saturated with the organic acid across the deselectivated catalyst for a period of time ranging from about 1 hour to about 20 hours. During contact with the acid vapors the catalyst is maintained at a temperature of from about 0° C. to about 100° C., preferably at from 15° C. to 100° C. and most preferably at a temperature of between 20° C. and 50° C.

When treatment is carried out using liquid organic acid, the deselectivated catalyst is immersed in the acid for from 5 minutes to 24 hours at a temperature as recited above with respect to vapor phase treatment. The liquid may comprise substantially pure organic acid (e.g. glacial acetic acid) or may contain diluents or carriers admixed with the acid. Examples of diluents utilizable for this purpose would include aromatic and non-aromatic hydrocarbons, alcohols, water, dimethylformamide, and other liquid materials which are inert with respect to the acid and the zeolite. After immersion for a sufficient period of time to rejuvenate the catalyst, the liquid is removed and the catalyst dried at from about 90° C. to about 150° C. to remove all traces of the liquid.

The organic acids utilizable in the process of this invention are those carboxylic acids having from 2 to about 5 carbon atoms. The acids may be linear, such as acetic, propanoic, butanoic and pentanoic acids, or may be branched, such as 2-methylpropanoic, 2,2-dimethylpropanoic, 2-methylbutanoic and 3-methylbutanoic acids. The anhydride form of such acids may also be employed. A preferred embodiment of the invention contemplates the treatment of the modified zeolite with acetic acid.

Subsequent to the foregoing treatment with organic acid, the reselectivated Mg/P modified catalyst may be calcined in the usual manner. After calcining, the catalyst will be rejuvenated to a substantially improved level of para selectivity and may be used in the same manner as the fresh catalyst.

In a preferred embodiment, the entire rejuvenation procedure is carried out in situ, that is without removing the catalyst from the reactor. In another embodiment, organic acid may be periodically mixed with the reactant feed stream, thereby reselectivating the catalyst at the first signs of reduced selectivity without having to shut down the entire reactor.

Another embodiment involves upgrading or increasing the selectivity of Mg/P modified catalysts which exhibit only moderate para selectivty. Such catalysts are defined as those which, after normal preparation and calcining, exhibit a threshold selectivity to the desired para isomer of approximately 80% to 92% relative to the sum total of the three possible isomers (ortho, meta and para). By treating such moderately selective catalysts as outlined above, it is frequently possible to increase their desirable para selectivity to a significantly higher and more useful level, for instance to about 90% to 96% of the isomeric product mix. This embodiment may be conveniently referred to as "selectivation" as opposed to "rejuvenation" or "reselectivation" of the catalyst.

The following examples will serve to illustrate the hereindisclosed invention. These examples should not, however, be construed as limiting the scope of the novel rejuvenation and selectivation process as there are many variations which may be made thereon without departing from the spirit of the disclosed invention, as those of skill in the art will recognize.

EXAMPLE 1

A ZSM-5/Al$_2$O$_3$ catalyst (65 wt % ZSM-5; 35 wt % Al$_2$O$_3$), which had been modified with phosphorus and magnesium so that the catalyst held 2.67 wt % P and 7.1 wt % Mg, was placed in a reactor at 425° C. and 100 psig. A feed stream of toluene, ethylene and H$_2$ was passed over the catalyst bed at feed WHSV of 30.0/1.15/0.25, respectively, and the effluent analyzed for ethylation of the toluene. Conversion of toluene was 9.5%, with 90% para ethyltoluene in the ethyltoluene product.

The catalyst was then deselectivated by lowering the reactor to ambient temperature and passing moist air across the catalyst for 14 hours. The catalyst was then calcined at 425° C. for 1.5 hours and tested for ethylation of toluene as before. Toluene conversion was 10.5%, with 62% selectivity to para-ethyltoluene.

The deselectivated catalyst was then subjected to acetic acid treatment (vapor phase) as follows:

A stream of air at 200 cc/min was passed through a reservoir of liquid acetic acid and then into the reactor and across the deselectivated catalyst for a period of 14 hours at ambient temperature. The acetic acid treated catalyst was then heated to 425° C. and tested for ethylation of toluene as before. Toluene conversion was 10.2% (42.9% of theoretical), with 94% selectivity to the para isomer of ethyltoluene.

The rejuvenated catalyst was also tested for selectivity to para-ethyltoluene at atmospheric pressure and 400° C. The feed WHSV was 7.0 for toluene and 0.5 for ethylene. Toluene conversion was 18.3% (76.9% of theoretical), with 93% selectivity to para-ethyltoluene.

EXAMPLE 2

A ZSM-5/Al$_2$O$_3$ catalyst (65 wt % ZSM-5, 35 wt % Al$_2$O$_3$) having 2.67 wt % phosphorus and 7.1 wt % magnesium deposited thereon, was tested for ethylation of toluene at 400° C. and atmospheric pressure. The feed stream, consisting essentially of toluene and ethylene, was passed over the fresh catalyst at WHSV of 7.0 and 0.5, respectively. Conversion of toluene was 21% (88% of the theoretical conversion), with 92% para isomer in the ethyltoluene product.

The catalyst was then deselectivated as in Example 1 and calcined at 400° C. for 1.5 hours. The alkylation experiment was repeated, with the result that toluene conversion was 22.3% (93.7% of theory) and selectivity to para-ethyltoluene 53.9%.

The deselectivated catalyst was rejuvenated by treatment with acetic acid (liquid phase) as follows:

A 5.0 g portion of the deselectivated Mg.P.ZSM-5/Al$_2$O$_3$ catalyst was added to 10 ml of glacial acetic acid and maintained at room temperature for 5 minutes. The acetic acid was removed by filtration and the catalyst dried at about 100° C. The dried catalyst was returned to the reactor, calcined at 500° C. for 1 hour, and tested for ethylation of toluene at 400° C. and atmospheric pressure. Toluene conversion was 16.7% (70.2% of theory) and selectivity to the para isomer was 84.8%.

The catalyst was then treated with liquid acetic acid a second time, following the same procedure, and tested again. Toluene conversion was 16.7% (70.2% of theory) and selectivity 86.1%.

EXAMPLE 3

An experiment was conducted to test the effect of repeated deselectivation and rejuvenation on a Mg.P.ZSM-5 catalyst. The catalyst employed was the same as that of Example 1. After the first rejuvenation in vaporous acetic acid the catalyst was utilized for toluene ethylation at 400° C. and atmospheric pressure (WHSV toluene/ethylene=7.0/0.5) for 116 hours. The catalyst was deselectivated a second time followed by rejuvenation with acetic acid in air as in Example 1. After use for an additional 23 hours in the toluene/ethylene reaction it was deselectivated a third time followed by treatment with acetic acid in air. The rejuvenated catalyst was then tested for ethylation of toluene for another 96 hours. The results are summarized in Table I.

TABLE I

Repeated Rejuvenation of Mg.P.ZSM-5

| | Hours on Stream | Toluene Conversion | Selectivity to para isomer in ethyltoluene |
|---|---|---|---|
| Fresh Catalyst | 1 | 9.5%* | 90% |
| Deselectivated in H$_2$O-Air | 1 | 10.5%* | 62% |
| 1st Rejuvenation in HOAc-Air | 0.5 | 18.3%** | 93% |
| | 1 | 10.7%** | 92% |
| | 19 | 10.2%** | 94% |
| | 43 | 9.9%** | 94% |
| | 81 | 9.2%** | 94% |
| | 116 | 7.9%** | 95.5% |
| Deselectivated in H$_2$O-Air | 1 | 11.5%** | 68% |
| 2nd Rejuvenation in HOAc-Air | 1 | 10.4%** | 84% |
| | 23 | 9.8%** | 82% |
| Deselectivation followed by 3rd rejuvenation in HOAc-Air | 1 | 9.3%** | 84.5% |
| | 23 | 9.8%** | 83.5% |
| | 46 | 8.9%** | 83.5% |
| | 73 | 8.5%** | 84% |
| | 96 | 8.1%** | 85% |

NOTES:
*All runs were made under the following conditions: Runs at 425° C., 100 psig, WHSV Toluene/ethylene/H$_2$ = 29.9/1.15/0.25. Theoretical maximum toluene convesion 12.5%.
**Runs at 400° C., atmospheric pressure and WHSV toluene/ethylene = 7/0.5. Theoretical maximum toluene conversion is 23.8%.

As will be seen from the foregoing experiment, the repeated reselectivation of a para selective catalyst which has been deselectivated by contact with moisture is quite feasible. With optimization of conditions, even better results should be possible.

EXAMPLE 4

A sample of a Mg.P.ZSM-5/Al$_2$O$_3$ catalyst which had become deselectivated in normal use was tested to demonstrate the effect of coking on the reselectivation of the catalyst. The catalyst consisted of 65 wt % ZSM-5 on Al$_2$O$_3$ and contained 2.67 wt % phosphorus and 7.1 wt % magnesium. The used catalyst was divided into two portions and treated as follows:

The first portion was regenerated by calcining in air at 500° C. for 14 hours to burn off the coke. It was then tested for disproportionation of toluene at 500° C., atmospheric pressure, by passing a feed stream of toluene over the regenerated catalyst at WHSV of 3.5. The temperature was then dropped to 400° C. and the feed stream changed to toluene/ethylene (WHSV 7.0/0.5, respectively) for ethylation of toluene. The regenerated catalyst was then returned to room temperature and rejuvenated by passing acetic acid in air across the catalyst bed for 14 hours. After calcining the regenerated catalyst at 500° C. in N$_2$ for 2 hours it was again tested for toluene disproportionation and alkylation as before. The results are summarized in Table II.

The second portion was not regenerated to remove the coke. Rejuvenation with acetic acid in air was carried out in the same manner as with the first portion. The rejuvenated catalyst, still containing the coke deposited in the normal use, was tested for disproportionation and ethylation of toluene as above. These results are also shown in Table II.

TABLE II

| | Toluene Disproportionation* | | Ethylation | |
|---|---|---|---|---|
| | Toluene Conversion | para-Xylene in Xylenes | Toluene Conversion | Selectivity to para isomer |
| 1st Portion: | | | | |
| Regenerated | 1.6% | 38% | 17.7% | 65% |
| HOAc-Air Rejuvenation | 1.5% | 43.5% | 15.8% | 75% |
| 2nd Portion: | | | | |
| HOAc-Air Rejuvenation of coked catalyst | 1.8% | 44% | 15.9% | 75% |

*Theoretical maximum toluene conversion is 23.8%.

As will be seen, normal regeneration does not rejuvenate the selectivity of the catalyst. Subsequent treatment with acetic acid was significantly increased the selectivity of the regenerated catalyst. However, as the results of the treatment of the second portion of the catalyst show, it is not necessary to burn the accumulated coke deposits from the zeolite to realize the benefit of the present invention. Acetic acid treatment of the non-regenerated (i.e. coked) catalyst shows substantially the same improved level of para selectivity as achieved by the catalyst which had been regenerated prior to rejuvenation with acetic acid.

EXAMPLE 5

The ability of the disclosed acetic acid treatment to increase the selectivity of only moderately selective Mg.P modified catalyst was demonstrated on a Mg.P.ZSM-5/Al$_2$O$_3$ (65 wt % ZSM-5 containing 4.1 wt % phosphorus and 4.3 wt % magnesium) which showed only 69.5% selectivity to para xylene in toluene disproportionation and 91% selectivity to para isomer in ethylation of toluene. After calcining at 500° C. in N$_2$ for 2 hours followed by acetic acid-air treatment at ambient temperature for 2 hours, the toluene disproportionation reaction showed 84.5% selectivity to para xylene and ethylation resulted in 96% para isomer in ethyltoluenes. The results and run conditions are summarized in Table III.

TABLE III

Selectivation of Moderately Selective Catalyst

| | Disproportionation* | | Ethylation** | |
|---|---|---|---|---|
| | Toluene Conversion | para-Xylene in Xylenes | Toluene Conversion | Selectivity to para isomer |
| Fresh catalyst | 11.0% | 69.5% | 16.2% | 91% |
| HOAc Treated catalyst | 4.7% | 84.5% | 17.5% | 96% |

NOTES:
*Disproportionation at 500° C., atmospheric pressure, toluene WHSV = 3.5
**Ethylation at 400° C., atmospheric pressure, toluene/ethylene WHSV = 7.0/0.5. Theoretical maximum toluene conversion is 23.8%.

What is claimed is:

1. In a process whereby aromatic hydrocarbon reactants are catalytically converted via alkylation, to a dialkylbenzene product containing the para-dialkylbenzene isomer of said product in a reaction zone under aromatic hydrocarbon conversion conditions in the presence of a catalyst comprising a crystalline zeolite having a Constraint Index within the approximate range of 1 to 12 and a silica to alumina mole ratio of at least 12, said zeolite being chemically modified by incorporation thereinto of a para-selectivity-enhancing oxide compound, the improvement which comprises:

effecting reselectivation of said catalyst, to restore catalytic para-selectivity which has diminished during conversion of said aromatic hydrocarbon reactants, by contacting said chemically modified, zeolite-based catalyst with a carboxylic acid or an anhydride thereof at a temperature of between about 0° C. and 100° C., after said para-selectivity diminishing conversion has occurred.

2. The process of claim 1 wherein said carboxylic acid has from 2 to 5 carbon atoms.

3. The process of claim 2 wherein the anhydride form of said carboxylic acid is utilized.

4. The process of claim 2 wherein said carboxylic acid is acetic acid.

5. The process of claim 1 wherein said temperature is between about 15° C. and 100° C.

6. The process of claim 1 wherein said temperature is between about 20° C. and 50° C.

7. The process of claim 1 wherein said zeolite is ZSM-5.

8. The process of claim 1 wherein said zeolite additionally comprises a binder therefor.

9. The process of claim 1 wherein said catalyst-modifying, para-selectivity-enhancing oxide compound is an oxide of phosphorus.

10. The process of claim 1 wherein said catalyst-modifying, para-selectivity-enhancing oxide compound is an oxide of an element selected from antimony, arsenic, boron, calcium, magnesium, nickel, uranium and zinc.

11. The process of claim 1 wherein said chemically-modified, zeolite-based catalyst is further reselectivated by heating said catalyst to a temperature of between about 250° C. and about 650° C. after contact of said catalyst with said carboxylic acid or anhydride thereof and prior to reuse of said reselectivated catalyst in promoting additional conversion of aromatic hydrocarbons.

12. In a process whereby aromatic hydrocarbon reactants are catalytically converted via alkylation, to a dialkylbenzene product containing the para-dialkylbenzene isomer of said product in a reaction zone under aromatic hydrocarbon conversion conditions in the presence of a catalyst comprising zeolite ZSM-5, said ZSM-5 zeolite being chemically modified by incorporation thereinto of a para-selectivity-enhancing oxide compound selected from phosphorus oxide, magnesium oxide, and combinations of phosphorus oxide and magnesium oxide, the improvement which comprises:

effecting reselectivation of said catalyst, to restore catalytic para-selectivity which has diminished during conversion of said aromatic hydrocarbon reactants, by contacting said chemically modified, ZSM-5-based catalyst with acetic acid at a temperature of between about 0° C. and 100° C., after said para-selectivity diminishing conversion has occurred.

13. In a process whereby aromatic hydrocarbon reactants are catalytically converted via alkylation, to a dialkylbenzene product containing the para-dialkylbenzene isomer of said product in a reaction zone under aromatic hydrocarbon conversion conditions in the presence of a catalyst comprising a crystalline zeolite having a Constraint Index within the approximate range of 1 to 12 and a silica to alumina mole ratio of at least 12, said zeolite being chemically modified by incorporation thereinto of a para-selectivity-enhancing oxide compound, the improvement which comprises:

effecting enhancement of the inherent para-selectivity of said catalyst by contacting said chemically modified, zeolite-based catalyst with a carboxylic acid or an anhydride thereof at a temperature between about 0° C. and 100° C., prior to utilizing said catalyst to promote conversion of said aromatic hydrocarbon reactants.

14. The process of claim 13 wherein said carboxylic acid has from 2 to 5 carbon atoms.

15. The process of claim 14 wherein the anhydride form of said carboxylic acid is utilized.

16. The process of claim 14 wherein said carboxylic acid is acetic acid.

17. The process of claim 13 wherein said temperature is between about 15° C. and 100° C.

18. The process of claim 13 wherein said zeolite is ZSM-5.

19. The process of claim 13 wherein said catalyst-modifying, para-selectivity-enhancing oxide compound is selected from an oxide of phosphorus, an oxide of magnesium and combinations of an oxide of phosphorus and an oxide of magnesium.

20. The process of claim 13 wherein the inherent para-selectivity of said chemically-modified, zeolite-based catalyst is further enhanced by heating said catalyst to a temperature of between about 250° C. and about 650° C. after contact of said catalyst with said carboxylic acid or anhydride thereof and prior to use of said catalyst in promoting conversion of aromatic hydrocarbons.

* * * * *

UNITED STATES PATENT AND TRADEMARK OFFICE
CERTIFICATE OF CORRECTION

PATENT NO.  : 4,486,616

DATED       : December 4, 1984

INVENTOR(S) : Chin-Chiun Chu and Warren W. Kaeding

It is certified that error appears in the above-identified patent and that said Letters Patent is hereby corrected as shown below:

Column 6, Lines 25-40, Table — Under heading "Void Volume" the entire column under "cc/cc" should be listed under "Framework Density".

Signed and Sealed this

Twenty-fifth Day of June 1985

[SEAL]

Attest:

DONALD J. QUIGG

Attesting Officer

Acting Commissioner of Patents and Trademarks